(12) United States Patent
Rastegar et al.

(10) Patent No.: US 9,084,622 B2
(45) Date of Patent: Jul. 21, 2015

(54) AUTOMATED LASER-TREATMENT SYSTEM WITH REAL-TIME INTEGRATED 3D VISION SYSTEM FOR LASER DEBRIDEMENT AND THE LIKE

(75) Inventors: Jahangir S. Rastegar, Stony Brook, NY (US); Thomas Spinelli, East Northport, NY (US)

(73) Assignee: OMNITEK PARTNERS LLC, Ronkonkoma, NY (US)

( * ) Notice: Subject to any disclaimer, the term of this patent is extended or adjusted under 35 U.S.C. 154(b) by 1861 days.

(21) Appl. No.: 11/888,813

(22) Filed: Aug. 2, 2007

(65) Prior Publication Data

US 2008/0033410 A1 Feb. 7, 2008

Related U.S. Application Data

(60) Provisional application No. 60/835,024, filed on Aug. 2, 2006.

(51) Int. Cl.
*A61B 19/00* (2006.01)
*A61B 18/20* (2006.01)
*A61B 17/00* (2006.01)
*A61B 18/00* (2006.01)

(52) U.S. Cl.
CPC ............. *A61B 19/2203* (2013.01); *A61B 18/20* (2013.01); *A61B 18/203* (2013.01); *A61B 19/5212* (2013.01); *A61B 2017/00707* (2013.01); *A61B 2018/00452* (2013.01); *A61B 2018/00636* (2013.01); *A61B 2018/00904* (2013.01); *A61B 2019/5272* (2013.01)

(58) Field of Classification Search
USPC ................... 606/9, 10, 13, 15, 35; 607/88, 89
See application file for complete search history.

(56) References Cited

U.S. PATENT DOCUMENTS

| | | | | |
|---|---|---|---|---|
| 5,865,828 | A * | 2/1999 | Jeng | 606/2 |
| 6,156,030 | A * | 12/2000 | Neev | 606/10 |
| 6,165,170 | A * | 12/2000 | Wynne et al. | 606/9 |
| 6,588,900 | B1 * | 7/2003 | Le Gargasson et al. | 351/200 |
| 6,918,905 | B2 * | 7/2005 | Neuberger | 606/9 |
| 7,083,611 | B2 * | 8/2006 | Lemchen | 606/9 |
| 2003/0181893 | A1 * | 9/2003 | Neuberger | 606/9 |
| 2006/0085053 | A1 * | 4/2006 | Anderson et al. | 607/94 |
| 2006/0276860 | A1 * | 12/2006 | Ferren et al. | 607/88 |
| 2008/0051773 | A1 * | 2/2008 | Ivanov et al. | 606/12 |

\* cited by examiner

*Primary Examiner* — Tuan V Nguyen

(57) ABSTRACT

A method for automated treatment of an area of skin of a patient with laser energy. The method including: identifying the area to be treated with the laser; modeling the identified area of the skin to be treated; and controlling the laser to direct laser energy to within the modeled area of the skin.

20 Claims, 10 Drawing Sheets

AUTOMATED LASER-TREATMENT SYSTEM WITH REAL-TIME INTEGRATED 3D VISION SYSTEM FOR LASER DEBRIDEMENT AND THE LIKE

CROSS-REFERENCE TO RELATED APPLICATIONS

The present application claims priority to U.S. provisional patent application, Ser. No. 60/835,024, filed on Aug. 2, 2006, the entire contents of which is incorporated herein by reference.

BACKGROUND OF THE INVENTION

1. Field of the Invention

The present invention relates generally to automated control of a laser head for treatments on human skin, and more particularly to automated control of a laser head for laser debridement of burns.

2. Prior Art

Thermal burns and vesicating (blistering) due to chemical warfare agents such as sulfur mustard and Lewisite induced skin injuries can vary in severity between second degree and third degree. Vesicant injuries in particular can take several months to heal, necessitating lengthy hospitalizations, and result in significant cosmetic and/or functional deficits.

The initial step in the repair of a thermal or chemical burn wound is to remove the dead skin, called wound debridement, and replaces it with a viable biological dressing. Autologous skin from another site of the patient, in the form of a split thickness skin graft is the method of repair that is most often employed. In special circumstances a flap of muscle with its attached blood supply may be used to cover severely burned areas that lack sufficient blood supply to allow the split thickness graft to become engrafted.

It has been shown that early excision at less than one week after the burn significantly reduces blood loss. Later excisions after 7-10 days are associated with significantly greater blood loss. The reason for this is that the very presence of the dead skin causes an inflammatory reaction which results in a significant increase in blood flow to the skin. Consequently, when burned skin is excised from the body after 7-10 days there is a much greater blood loss. Others have analyzed the survival rates after burns over a 50 year period and concluded that prompt excision of the eschar after the burn occurred was largely responsible for reducing the mortality after burns, and resulted in a significant improvement of survival rate.

It is, therefore, apparent that early excision of the burn and immediate coverage of the wound with a biologic dressing, preferably autologous skin, if it is available, is the optimal method for caring for the thermal and chemical burn wound.

There are various methods of wound debridement. The method of wound debridement that is most commonly used is surgical excision using stainless steel cutting blades, which can be mounted on different types of handles and into which are built methods of controlling the depth of the excision. The excision may be superficial, as in a deep dermal burn, by cutting off the injured tissue through the appropriate level of the dermis; or in the case of a full thickness burn, the entire skin: i.e., epidermis and dermis may be cut off either leaving the subcutaneous tissue or the fascia exposed. This method of using a steel blade as a cutting instrument works well in the hands of a well trained surgeon. However this method is time consuming in large burns and is often associated with the loss of considerable amounts of blood. The least amount of blood is lost when the entire thickness of skin and subcutaneous tissue must be excised. The reason for this, is that in this setting the individual blood vessels arising from the deeper tissues can be identified and can be ligated before they enter the skin. Whereas excisions through either superficial or deeper dermis are associated with significantly more bleeding, since the distinct nutrient vessels which arise from the deeper tissues have arborized into numerous branches as they progress towards the surface of the skin.

Until recently, the standard method for burn debridement, as stated earlier has been the use of stainless steel blades. Recent advances have been made in improving the healing of thermal and chemical burns using a variety of techniques to debride damaged tissue, including the use of medical lasers. One promising modality for excision (debridement) uses a laser beam. Excision using a laser beam would be associated with significantly reduced morbidity, since the amount of blood lost when a laser beam is used has been shown to be significantly reduced. It is important to note also that the percentage of successful wound closures after the excision using grafts is the same irrespective of whether a laser or a steel knife was used to remove the eschar. Laser vaporization of full thickness burn eschar in a porcine model with immediate engraftment was shown to be associated with minimal blood loss and equal graft take.

Current uses of lasers in dermatological practice as well as the types of lasers used for each specific procedure are well known. They include $CO_2$ and Er:YAG lasers as being the most appropriate for cutaneous resurfacing.

The $CO_2$ laser emits radiation at a wavelength of 10,600 nm. The fluence should exceed the vaporization threshold of skin (5 J/cm$^2$)[4,5] and the pulse duration (or its scanning laser equivalent, the 'dwell time') should be shorter than the $\tau$ (695-950 ms) although pulse widths of up to 1 ms appear to be acceptable in vivo. At lower fluences there is more desiccation and carbonization and a higher likelihood of scarring. The depth of vaporization and thermal necrosis depend on the fluence, dwell time and number of passes. Two different laser systems are in common use. High energy pulsed lasers produce wide diameter pulses with beam diameters of up to 3 mm. A computerized pattern generator can be used in the treatment of relatively large areas. With low energy scanned focused beams, a computer-controlled mirror rapidly scans a focused beam across a predetermined area. The dwell time is 300-900 ms depending on the depth of damage required. Clinical outcomes using these two different types of system can only be compared if the fluences and number of passes are considered.

The Er:YAG (erbium:yttrium-aluminium-garnet) lasers produce radiation ($\lambda$=2940 nm) with a higher absorption coefficient for water than the $CO_2$ laser and a lower optical penetration depth (1 µm and 20 µm, respectively). Because ablation is inversely proportional to the optical penetration depth, Er:YAG lasers require a lower fluence for tissue ablation. This is a largely photoacoustic rather than a photothermal reaction. The depth of vaporization is 2-4 µm for each 1 J/cm$^2$ fluence and very superficial peels may be achieved. Epidermal lesions can be ablated accurately, but deeper peels may be limited by intraoperative bleeding due to the relatively thin layer of residual thermal damage. Attempts to improve haemostasis have been made by adapting the Er:YAG laser to produce longer pulses and/or lower fluences or through combination with low-fluence $CO_2$ or with secondary Er:YAG lasers. Side-by-side comparisons suggest that for the same depth of injury, re-epithelialization time and persistence of erythema is shorter in sites treated with the Er:YAG as opposed to the $CO_2$ laser. However, the thickness of subsequent fibrosis or 'collagen remodeling' is greater in $CO_2$ laser-treated sites, possibly reflecting greater underlying thermal damage.

Er:YAG lasers have been used for a wide variety of procedures, ranging from facial resurfacing to burn debridement. They have been shown to be particularly useful in the debridement of partial-thickness thermal burns and in the management of deep Lewisite injuries. A review of the literature clearly indicates that laser debridement produced equally good results with excisions performed with a steel blade. In addition, unlike the Gaussian beam profiles created by $CO_2$ lasers, Er:YAG laser beams tend to be uniform and produce uniform depths of ablation. Thus, it can be concluded that the use of erbium:yttrium-aluminum garnet (Er:YAG) laser in the skin resurfacing to debridement of deep partial thickness burns, including those caused by sulfur mustard have demonstrated benefits of this method of excision.

It is noted that debridement with Er-YAG and $CO_2$ lasers promise to provide great benefits in the treatment of leg ulcers (e.g., venous stasis ulcers, pressure ulcers, diabetic foot ulcers). Additionally, leg ulcers (e.g., venous stasis ulcers, pressure ulcers, diabetic foot ulcers) and penetrating injuries to the skin can require frequent debridement to help these wounds to heal.

Lasers have a wide range of applications in dermatology. Such procedures include removal of hair, tattoos, freckles, wrinkles, acne, sun-damaged skin, scars—including surgical and acne scarring, facial red veins and other vascular lesions, skin resurfacing and malformations (such as port wine stains) and hair and tattoo removal. Lasers are also being used or investigated for removal of keloids and hypertrophic scars as well as viral warts, seborrhoeic keratoses, skin cancers, and psoriasis plaques.

One major drawback of all currently available laser systems is that they require the physician and/or surgeon to move a hand piece over the damaged area, which is very time-consuming given an injury with a large surface area. The process also requires a skilled physician/surgeon, and a steady hand. The design of small hand held scanners on the ends of articulated arms has weakened this drawback to a limited extent. However, the scanned areas are relatively small and the physician/surgeon still needs to move the scanner head over relatively large treatment areas. A time savings could be realized with a system that could scan very large areas of a patient's body and perform precise laser treatment, such as debridement automatically and quickly with minimal physician/surgeon/technician involvement. In fact, certain laser treatment processes are so slow that they are effectively impractical for treating patients. This is the case, for example, for erbium:YAG lasers used for laser debridement of chemical and thermal burn injuries. For the latter applications, such a system would greatly decrease medical logistical burden, especially in a mass casualty scenario.

In the present disclosure, the various embodiments of the present invention are described in terms of their application for laser debridement of chemical or thermal burns. However, it is appreciated by those familiar with the art that the described embodiments can also be used as automated systems for a number of other skin treatments such as for removal of hair, tattoo, freckle, wrinkle, acne, sun-damaged skin, acne scarring facial red veins and other vascular lesions and malformations (such as port wine stains) with minimal effort. Such lasers treatments have also shown great promise for removal of keloids and hypertrophic scars as well as viral warts, seborrhoeic keratoses, skin cancers and psoriasis plaques.

It is also appreciated by those skilled in the art that the described embodiments of the present invention are modular in design so that each component of the system and its operating software could be readily updated and upgraded.

SUMMARY OF THE INVENTION

A need therefore exists for automated laser treatment systems that require minimal physician/surgeon/technician interaction during the treatment and after the physician/surgeon/technician or appropriate medical personnel has indicated the treatment area(s) and set the operating parameters of the system.

There is also a need for automated and precision laser treatment systems to achieve precision and speedy treatment of patients, particularly when large areas have to be treated. Such a precision and automated system would allow a significant amount of time saving to be achieved with a system that could scan very large areas of a patient's body and perform precise debridement automatically and quickly with minimal physician/surgeon involvement.

There is also a need for automated laser debridement systems for the treatment of chemical and thermal burn injuries to significantly reduce medical logistical burden, especially in a mass casualty scenario.

There is also a need for automated and precision laser treatment systems that could be operated by medical personnel under the supervision of a remotely located specialized surgeon, especially in a mass chemical burn casualty scenario.

Accordingly, a novel method is provided that could be used to develop automated laser treatment systems for the treatment of wide varieties of skin and other ailments of exposed body surfaces, such as the aforementioned chemical and thermal burn debridement and other dermatological conditions that are treatable with laser or other light sources.

The present automated laser treatment systems and methods for cutaneous conditions and injuries and other similar laser treatment applications comprises one or more of the following components:

1. A multi-purpose near real-time 3D vision system for scanning the indicated area(s) on the surface of the patient body. The vision system is used for 3D measurement of the indicated area(s) on the surface of the patient body and development of a 3D map of the said area(s); to track the actual position of the laser head at all times, particularly during the laser treatment; to continuously and in real-time update the 3D map of the indicated area(s) in case of the patient movement or geometrical variations in the surface area(s); to continuously and in real-time update the 3D map of the indicated area(s) and its location relative to the laser head (robot end-effector when a robot is used to position the laser head), in case of the patient movement and geometrical variation in the treatment surfaces or unwanted movement of the laser head, for example due to an accidental running into its support structure; to continuously and in real-time monitor the actual position of the treating laser spot(s) over the indicated treatment area(s) and comparing it with the planned positioning of the said treating laser spot(s) and calculating the positioning error of the said treating laser spot(s) and providing it to the system controller to affect corrective action or if the error is beyond a selected threshold, to shut down the treatment process for safe operation of the system; and to provide and update the map of treated surfaces and the number of passes and the corresponding system parameters set by the physician/ surgeon or the medical personnel and automatically by the system as a record of patient treatment. For this purpose, a number of vision systems are currently available and could be used. For example, one may use the real-time 3D surface shape measurement system based on a digital fringe projection and phase-shifting technique as described in the U.S. Pat. Nos. 6,788,210 and 6,438,272 can be used.

2. The system may be designed in the following two basic system configurations using either a robotic arm to provide the means to scan the treatment surface (with or without a pattern scanning laser heads), or using a programmable large-area laser scanning system:
   a. Embodiment with a robotic arm: In this embodiment, the Er:YAG laser head is attached to the terminal link of the robot manipulator and constitutes its end-effector. In general, the robot can have a minimum of 5 degree-of-freedom to be capable of positioning and orienting the laser beam over the treatment area of arbitrary topology. However, for the treatment of more uniform and relatively smaller surfaces, robotic arms with fewer degrees-of-freedom may be used. The robot arm must also be dexterous enough within its intended workspace to cover the maximum treatment surface without patient and/or machine movement.
   b. Embodiment with a programmable, large-area laser scanning system.
3. A system for removing smoke and fumes generated during the treatment and filtering and collecting the generated residue for disposal.
4. A computer based central control unit with touch-screen monitor or the like. The system would preferably allow the physician to interactively circumscribe the treatment areas on the monitor screen, and enters operating parameters of the laser. The physician may, for example, subdivide the treatment areas for different treatment parameters and even lasers and number of passes.
5. A computer vision system that can automatically determine the treatment area, such as the burned area, scarred area, tattoo, etc. and control the laser head accordingly.

BRIEF DESCRIPTION OF THE DRAWINGS

These and other features, aspects, and advantages of the apparatus and methods of the present invention will become better understood with regard to the following description, appended claims, and accompanying drawings where:

DETAILED DESCRIPTION OF THE PREFERRED EMBODIMENTS

Figure 1:
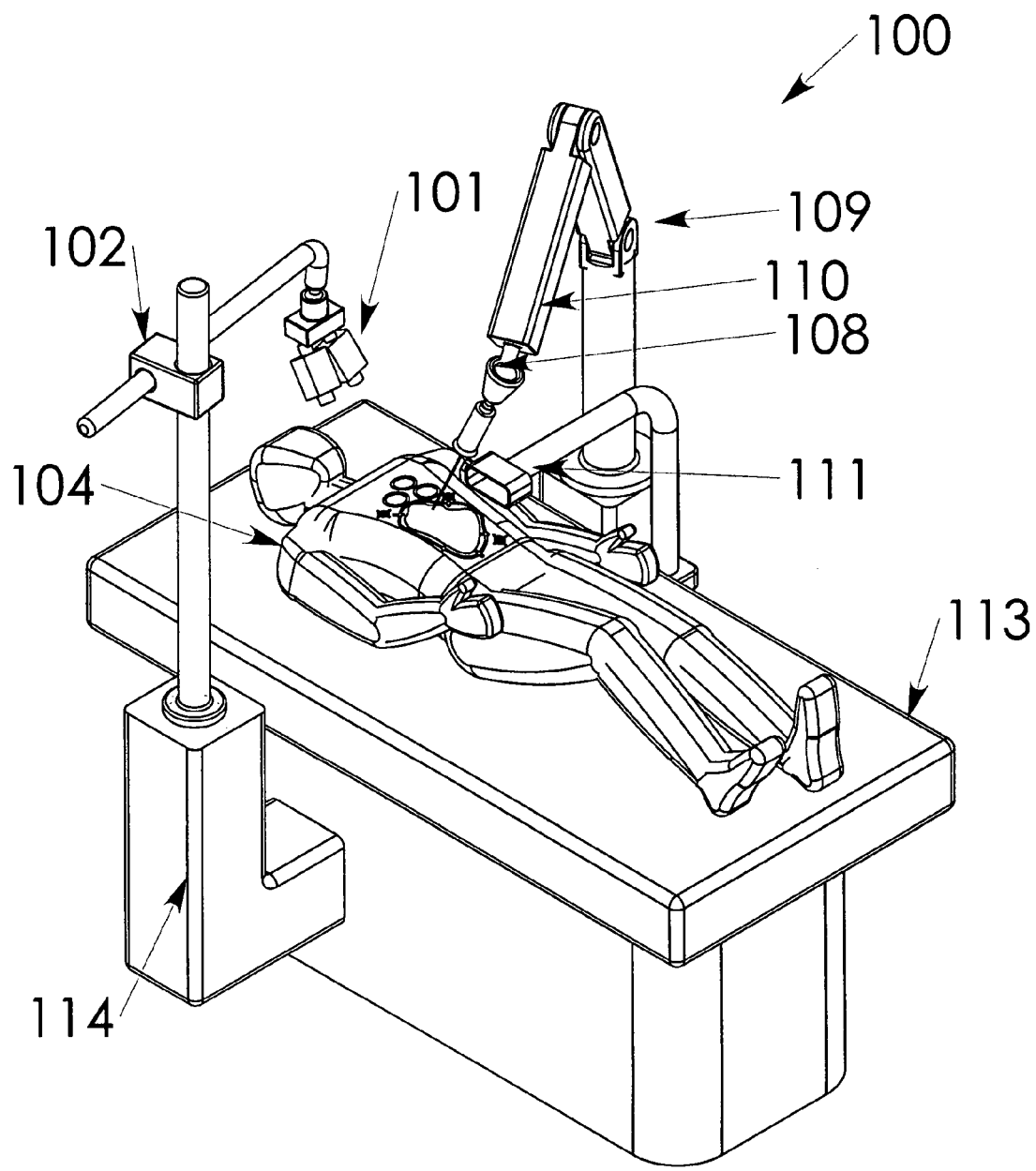
FIG. 1 illustrates a schematic of an embodiment of an automated laser treatment system.

The characteristics of disclosed embodiments of the present automated (Er-YAG or other) laser debridement and for cutaneous injuries are as follows:
   a. The physician or medical technician will identify the general areas within which the treatment areas are positioned using a simple marker. Alternatively, a computer vision system will identify the burned tissue due to differences between the burned tissue and healthy tissue that are recognizable by the vision system. An appropriate vision system, such as the aforementioned high resolution and near real-time 3D surface mapping vision system, generates a 3D map of the circumscribed areas, preferably together with their color and texture, and displays the generated images on a touch-screen monitor. Two or more tick marks along the circumscribing curves can be used for more accurate and faster calculation of the relative positioning of the 3D surfaces relative a fixed reference system. This reference system can be fixed to the 3D surface mapping vision system to minimize measurement errors. It is, however, appreciated by those familiar with the art that instead of the aforementioned tick marks, other marks, the circumscribing curves, landmarks on the treatment surface, or any other commonly used recognition algorithms and/or their combinations may also be used.
   b. The physician circumscribes the treatment areas on the touch-screen monitor and enters the operating parameters of the laser, including the number of passes over each region of the treatment areas.
   c. The system is capable of generating 3D maps of very large and multiple treatment areas over the patient's body using the aforementioned high-resolution and real-time 3D surface mapping vision system.
   d. The curve(s) circumscribing the general area(s) are used as landmarks (preferably with two or more tick marks on the curves or markers) to update the 3D maps of the treatment areas, and provide continuous sensory information indicating the position of the laser beam (and laser head and/or the robot arm with the embodiments using robot arms) relative to the treatment areas. This sensory information is used to close the feedback loop on the laser beam travel along its planned trajectory over the treatment area.
   e. The high-resolution and fast 3D surface mapping vision is used to continuously update the maps of the treatment areas to account for changes in their geometry as a result of patient movement or muscle actions, using the provided landmarks (the circumscribing curves, tick marks, markers, etc. used). In the embodiments using robot arms, the position of the laser head and the robot arm (preferably the terminal link to which the laser head is usually attached) is also updated continuously, preferably using three or more marked points on the laser head and the robot arm.
   f. For the embodiments that use robot arms, for additional safety and fine adjustments, matching calibration images may also be projected over the treatment area by the projector of the 3D surface mapping vision system and by image projectors mounted on the laser head. The vision system would then monitor the two images and determines the amount of adjustment in the position of the laser beam and robotic arm that is needed to overlay the two projected images. The system controller uses this information and the corresponding error information to close its feedback loop.

g. The actual position of the laser beam on the body surface is also monitored continuously by the 3D surface mapping vision system. Thereby providing at least one independent means of automatically monitoring its correct positioning and path of scanning in real time. This will be in addition to the health professional operating the proposed (e.g., Er-YAG laser debridement) system. In one embodiment, a second vision system is provided in addition to the aforementioned 3D surface mapping system with the primary purpose of continuously monitoring the position of the laser beam on the treatment area and comparing it with the desired position of the beam and directly providing a signal to the system controller to shut off the power to the treatment laser when an specified error threshold has been reached.

h. The disclosed automated system can scan large areas of the body that are in need of treatment such as wound debridement following a skin injury and perform the debridement with minimal surgeon involvement. For chemical and thermal burn debridement, the system preferably uses erbium:yttrium-aluminum-garnet (Er:YAG) laser and allows the attending physician to program the instrument to treat, such as debride specific areas of damaged tissue. Physicians will be able to interactively circumscribe the treatment areas on a video screen and enter operating parameters of the laser. The system will then quickly and automatically perform the debridement.

The disclosed embodiments of the "automated (e.g., Er-YAG or $CO_2$) laser debridement system" for cutaneous injuries, hereinafter referred to as ALDS, or for the laser treatment of other aforementioned conditions, hereinafter referred to as "automated laser treatment systems", ALTS, consist of the following three major hardware components:

1. A (preferably 3D) vision or other similar system for treatment surface measurements and/or recognition;
2. A laser source(s), e.g., an Er-YAG or $CO_2$ laser source alone in combination with one or more other laser sources;
3. Either a robotic arm or at least one wide-area scanning laser head.

The vision or other similar system for treatment surface measurements can be a 3D vision system, and can provide a high-resolution, fast, and near real-time 3D surface shape measurement and mapping, including mapping of curves and lines and points on the measured surfaces. One such system using a digital fringe projection and phase-shifting technique is described in the U.S. Pat. Nos. 6,788,210 and 6,438,272. A short description of this system together with its specific use for the various embodiments of the present invention is provided below. It is noted that as previously indicated, the description is provided by its application to Er:YAG lasers used for debridement, but the description is general and applicable to any one or combinations of lasers used for any treatment of exposed surfaces of the body.

The vision or other similar system can be multi-purpose, i.e., it will be used to: 1) scan the indicated area(s) for debridement; 2) develop a 3D map of the said surfaces, curves circumscribing the treatment areas, and the markings such as tick marks used for positioning indications; 3) track the Er:YAG laser head (when robots are used to move laser head) or track laser beams (when a scanning laser head is used alone) during the debridement; 4) continuously update the 3D map of the surfaces being treated to correct for changes in the 3D geometry of the surfaces due to muscle action, body movement, etc.; 5) when robots are used to move laser head, to continuously update the spatial position of the robot end-effector, i.e., the Er-YAG laser head, relative to the treatment surfaces; and 6) thereby provide the means to close the feedback loop for the Er-YAG laser scanning process of the indicated treatment areas. The vision system may also be used to recognize the areas to be treated, such as recognizing burned tissue as opposed to healthy tissue, recognizing scarred tissue, recognizing a tattoo to be removed, recognizing a port-stain, etc.

The operating system may also be used to continuously update the 3D map of the treatment areas with information regarding the treated regions and the number of passes in each region. The information may be stored in the patient file for future use.

The vision based system can be a high-resolution, real-time, 3D surface measurement system, which operates based on a digital fringe projection and phase-shifting technique. It utilizes a single-chip DLP projector to project computer generated fringe patterns onto the object and a high-speed CCD camera, which is synchronized with the projector to acquire the fringe images at a frame rate of 120 frames per second (fps). Based on a three-step phase-shifting technique, each frame of the 3D shape is reconstructed using three consecutive fringe images. Therefore the 3D data acquisition speed of the system is 40 fps. Together with the fast three-step phase-shifting algorithm and parallel processing software being used, the system provides high-resolution, real-time, 3D shape measurement at a frame rate of up to 40 fps and a resolution of 532×500 points per frame.

In addition, a color CCD camera can also be used to capture images for texture mapping over the aforementioned mapped surfaces. The availability of this feature in the vision system provides the means for further enhancement of the system to continuously monitor the effects of the Er-YAG laser scanning during the treatment and at certain periods of time post treatment.

Among all existing vision based surface mapping techniques, stereovision is probably the most studied and used method. Traditional stereovision methods estimate shape by establishing spatial correspondence of pixels in a pair of stereo images. A new concept called spacetime stereo has been developed, which extends the matching of stereo images into the time domain. By using both spatial and temporal appearance variations, it was shown that matching ambiguity could be reduced and accuracy could be increased. The shortcoming of spacetime stereo or any other stereo vision method is that matching of stereo images is time-consuming, therefore making it difficult to reconstruct high-resolution 3D shapes from stereo images in real time.

Another major group of vision based surface mapping techniques uses structured light, which includes various coding methods and employs varying number of coded patterns. Unlike stereo vision methods, structured light methods usually use processing algorithms that are much simpler. Therefore, it becomes possible to achieve real-time performance, i.e., measurement and reconstruction. For real-time shape measurement, there are basically two approaches. The first approach is to use a single pattern, typically a color pattern. The use of this approach employs a color-encoded Moire technique for high-speed 3D surface contour retrieval. Others have developed a rainbow 3D camera for high-speed 3D vision. Still others have developed a color structured light technique for high-speed scans of moving objects. Since the above methods use color to code the patterns, the shape measurement result is affected to varying degrees by the variations of the object surface color. In general, better accuracy is obtained by using more patterns. Thus, the above methods sacrifice accuracy for improved measurement speeds.

Another structured light approach for real-time shape measurement is the use of multiple coded patterns with rapid switching between them so that they could be captured in a short period of time. This approach has been used and develops a real-time 3D model measurement system that uses four patterns coded with stripe boundary codes. The acquisition speed achieved used was 15 fps, which is good enough for scanning slowly moving objects. However, like any other binary-coding method, the spatial resolution of these methods is relatively low because the stripe width must be larger than one pixel. Moreover, switching the patterns by repeatedly loading patterns to the projector limits the switching speed of the patterns and therefore the speed of shape measurement.

An example of a system for use with the present application is disclosed in U.S. Pat. Nos. 6,788,210 and 6,438,272 which provide a vision system for real-time and high-speed 3D shape measurement, with full capability of providing fast updating of the 3D surface maps and maps of the curves indicating the treatment areas and positioning markings such as tick marks of the said curves, thereby serving as the sensor to close the present automated debridement systems control loop and as the means to provide for safe operation of the system, by for example, shutting the treatment laser beam off when the error between the actual position and desired position of the treatment laser beam is more than a selected (programmed) threshold. This method is based on a rapid phase-shifting technique. This technique uses three phase-shifted, sinusoidal grayscale fringe patterns to provide pixel-level resolution. The patterns are projected to the object with a switching speed of 240 fps. This system takes full advantage of the single-chip DLP technology for rapid switching of three coded fringe patterns. A color fringe pattern with its red, green, and blue channels coded with three different patterns is created by a PC. When this pattern is sent to a single-chip DLP projector, the projector projects the three color channels in sequence repeatedly and rapidly. To eliminate the effect of color, color filters on the color wheel of the projector are removed. As a result, the projected fringe patterns are all in grayscale. A properly synchronized high-speed B/W CCD camera is used to capture the images of each color channel from which 3D information of the object surface is retrieved. A color CCD camera, which is synchronized with the projector and aligned with the B/W camera, is also used to take 2D color pictures of the object at a frame rate of 26.7 fps for texture mapping. Together with the fast 3D reconstruction algorithm and parallel processing software, high-resolution, real-time 3D shape measurement is realized at a frame rate of up to 40 fps and a resolution of 532×500 points per frame. Other systems for 3D shape measurement known in the art can also be used in the system and methods of the present invention, such as those commercially available from Blue Hill Optical Technologies, located in Norwood, Mass. or Nutfield Technology, Windham, N.H.

For the projection of the computer-generated patterns, a single-chip DLP projector is used, which produces images based on a digital light switching technique. With this system, a complex facial surface has been mapped at 40 fps (the accuracy of the system being 0.1×0.1×0.1 mm), providing an excellent speed and resolution for the present automated laser debridement and treatment systems and the like.

The color image is produced by projecting the red, green, and blue channels sequentially and repeatedly at a high speed. The three color channels are then integrated into a full color image. To take advantage of this projection mechanism of a single-chip DLP projector, a color pattern which is a combination of three patterns in the red, green, and blue channels is created. The projector has no color filters for a monochrome mode of operation. As a result, when the color pattern is sent to the projector, it is projected as three grayscale patterns, switching rapidly from channel to channel at 240 fps. A high-speed B/W camera, which is synchronized with the projector, is used to capture the three patterns rapidly for real-time 3D shape measurement. An additional color camera is used to capture images for texture mapping. To obtain 3D maps and color information simultaneously, multi-threading programming is used to guarantee that two cameras work independently and that the timing of image grabbing is only determined by the external trigger signal.

For more realistic rendering of the object surface, a color texture mapping method is used that is based on a sinusoidal phase-shifting method. In this method, the three fringe patterns have a phase shift of $2\pi/3$ between neighboring patterns. Since averaging the three fringe patterns washes out the fringes, a color image can be obtained without fringes by setting the exposure time of the color camera to one projection cycle or 12.5 ms.

The above system provides the capability of rapidly projecting and capturing three coded patterns rapidly. The employed fast three-step phase-shifting method provides a real-time 3D reconstruction speed and high measurement accuracy of the order of 0.1×0.1×0.1 mm. The sinusoidal phase-shifting method that has been used extensively in optical metrology to measure 3D shapes of objects at various scales. In this method, a series of phase-shifted sinusoidal fringe patterns are recorded, from which the phase information at every pixel is obtained. This phase information helps determine the correspondence between the image field and the projection field. Once this correspondence is determined, the 3D coordinate information of the object can be retrieved based on triangulation. A number of different sinusoidal phase-shifting algorithms are available. In the present system, a three-step phase-shifting algorithm similar to the traditional three-step algorithm is used, which requires three phase-shifted images.

In one embodiment, the automated Er-YAG laser debridement system uses a commercially available Er-YAG laser head and related system (such as the Profile Surgical Laser system from Sciton, Inc., Palo Alto, Calif.). In this system, the laser head is attached directly to the end-effector (e.g., the last free link) of a robot manipulator arm. The aforementioned 3D vision system camera and projector head is fixed to the patient bed structure. The patient is considered to be positioned on the bed in the appropriate posture to expose the treatment area to the vision system. In this system configuration, the vision system camera and projector unit is attached at a far enough distance from the treatment surface to allow a relatively large field of view to scan the patient body surface somewhat beyond the circumscribed treatment area(s) to allow for certain amount of body movement during the treatment.

It is noted that all available Er-YAG or other laser heads that are currently available are designed to be operated manually. For this reason, to allow the user to have more control as to the positioning of the laser head and thereby the laser spot over the treatment surface area, the laser heads are optically designed to be held a relatively short distance (mostly around 10-15 cm) from the treatment area. For this reason, the vision system camera and projector unit has to be positioned further away from the laser head and the treatment area to allow a large enough filed of view. As a result, the laser head and the 3D vision system camera and projector unit cannot be easily co-located at the end-effector of the robot.

Obviously in certain dermatology applications in which the treatment area is relatively small and can be captured well from a shorter 10-15 cm distance, then the 3D vision system camera and projector unit and the laser head component can be attached directly to the end-effector of the robot manipulator. Such a configuration is always preferred since the relative position of the vision system and the laser head is fixed and calibration and real-time control of this relative position does not have to be made before and during the treatment process.

Figure 2:
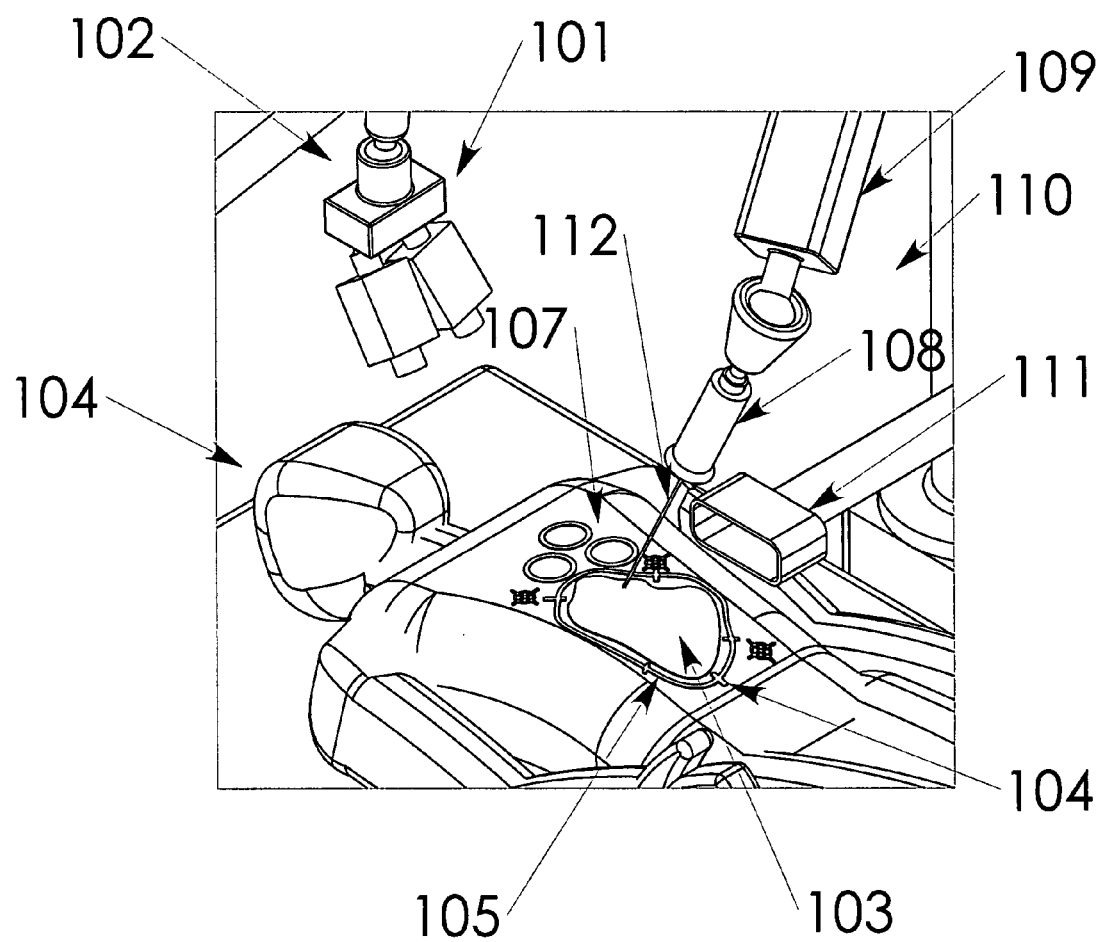
FIG. 2 illustrates a close up view of the treatment area and the main components of the system of FIG. 1.

The schematic of this automated Er-YAG laser debridement system design configuration 100 is shown in FIG. 1. A close up of the treatment area and the main components of the system is shown in FIG. 2. The 3D vision system 101 is shown to be attached to an adjustable stand 102 that is positioned in the proper view of the treatment area 103 of the subject 104. The treatment area 103 is clearly shown in FIG. 2 with its marked circumscribing curve 105 and several tick marks 106 to increase surface model position and orientation measurement accuracy. Additional markers such as the three small target markers 107 such as those shown in the close-up of FIG. 2 may be added to increase the vision system calibration distances. The three circles 107 above the treatment area are preferably projected by lights (not shown) fixed to the laser head 108, which is fixed to the end-effector 110 of the robot arm 109 and are used as secondary means to continuously calibrate the position of the laser head 108 (i.e., the robot arm 109) in the coordinate system of the 3D vision system 101.

A smoke evacuation vacuum head 111 is provided to evacuate the generated smoke and debris resulting from the debridement or other operations. Such smoke evacuation systems are well known in the art and may use air circulation to increase the efficiency of the evacuation system. The evacuated flow is usually filtered using appropriate filtering systems that are routinely cleaned and their filters replaced when such disposable filters are utilized.

This embodiment has the following configuration, characteristics, advantages and shortcomings relative to other embodiments described below:

1. A pattern scanning and currently available Er-YAG laser head 108 is preferably used. The use of pattern scanning laser heads would significantly reduce the demand on the robot arm 109 speed and precision. This is the case since the robot arm 109 need only position the laser head 108 at discrete positions over the treatment area 103 and allows the pattern scanning head to scan discrete areas, preferably slightly overlapping areas, to eventually cover the entire treatment area 103. That is, the robot arm 109 needs only to make the so-called point-to-point motions and is not required to perform the actual movement of the laser beam 112 over the treatment areas. One other advantage of using the said pattern scanning laser heads is that the robot arm 109 may be locked at each said positioning of the robot arm, thereby minimizing the effects of someone or some object bumping into the robot arm 109. One shortcoming of the use of currently available pattern scanning laser heads is that nearly all such devices provide only a limited choice on the available geometrical shape of the area that can be scanned, and it is therefore almost always impossible to fully cover treatment areas with complex geometries, particularly in areas that are not mostly flat and contain curved surfaces.

2. The aforementioned 3D vision system camera and projector unit 101 is preferably attached to an adjustable and locking vision system stand 102 as shown in FIGS. 1 and 2, and is positioned in a proper position prior to the start of treatment process to provide it with a good view of the treatment area 103. Proper positioning can be greatly facilitated by providing a projected target area onto the treatment surface area (not shown) similar to X-ray machines during this adjustment process. It is noted that in the schematics of FIG. 1 the adjustable vision system stand 102 is shown to be attached to the treatment bed 113 with an attachment structure 114. Alternatively, the adjustable vision system stand 102 may be a separate unit (not shown), preferably on locking wheels, that is positioned in an appropriate location by the medical personnel prior to treatment. The latter option is preferred when the treatment bed 113 is not dedicated solely for use with the present laser treatment system 100 and is used for other types of treatments as well.

3. At certain positions, the laser head 108 and/or the robot arm 109 may temporarily block the field of view of the 3D vision system 101. The blockage of the view, unless it blocks a significant portion of the treatment area 103 and the surface markers 104, 105 and 107, should not interfere with the proper operation of the system since from such partial views (and the view of the laser head markers—not shown) the 3D vision system 101 can determine the actual positioning of the laser spot over the blocked treatment area surfaces. To increase the level of safety even further, for relatively prolonged blockage of the areas being treated, the present system could be programmed to periodically stop the laser debridement process, move the laser head 108 away to expose the entire treatment area 103 and the surface markers 104, 105 and 107, update the treatment area surface model, and then resume the laser debridement process.

4. Since the position of the laser head 108 is not fixed relative to the 3D vision system camera and projector unit 101, before and on a regular time intervals during the laser debridement process, the position of the laser head 108 and the robot manipulator arm 109 relative to the 3D vision system 101 has to be determined as previously described and the information updated (adjusted) to eliminate any potential error accumulation.

5. Since the distance from the laser head 108 to the treatment surface 103 is relatively small, the laser head 108 can only scan a relatively small surface area with the indicated pattern. This means that the robot manipulator arm 109 must make a significant number of moves to cover a relatively large area.

6. Since the distance from the laser head 108 to the treatment surface 103 is relatively short, there is less chance of accidental reflections and/or running into the beam path by the medical personnel and the patient.

7. This system configuration would tolerate a relatively large movement of the patient 104 during the treatment.

8. The robot manipulator requires at least five degrees-of-freedom to allow the laser head 108 to be positioned anywhere over the indicated treatment area surfaces 103 and oriented perpendicular to the treatment surface within an appropriate range of approach angle. In most cases, an approach angle of around ±15 degrees or even larger would be acceptable since the resulting laser spot distortion and power density over the laser spot would be minimal. The scanning pattern generation capability of the laser head 108 is considered to be capable of handling any angular positioning of the laser head 108 about the laser beam 112 axis. Otherwise a sixth degree-offreedom has to be added to the robot manipulator arm 109 to allow for independent rotation of the laser head 108 about the general laser beam 112 axis to arbitrarily position the scanning pattern area over the treatment surface area 103. In many situations, however, particularly when relatively small and flat surfaces are being treated and since slight laser beam 112 deviation from the direction perpendicular to the treatment area is well tolerated due to the resulting small deviations from the designated laser spot and resulting power density, then as few as 3 degrees-of-freedom for robot arm 109 may be sufficient for positioning of the laser head 108 at discrete positions over the treatment area 103.

Figure 3:
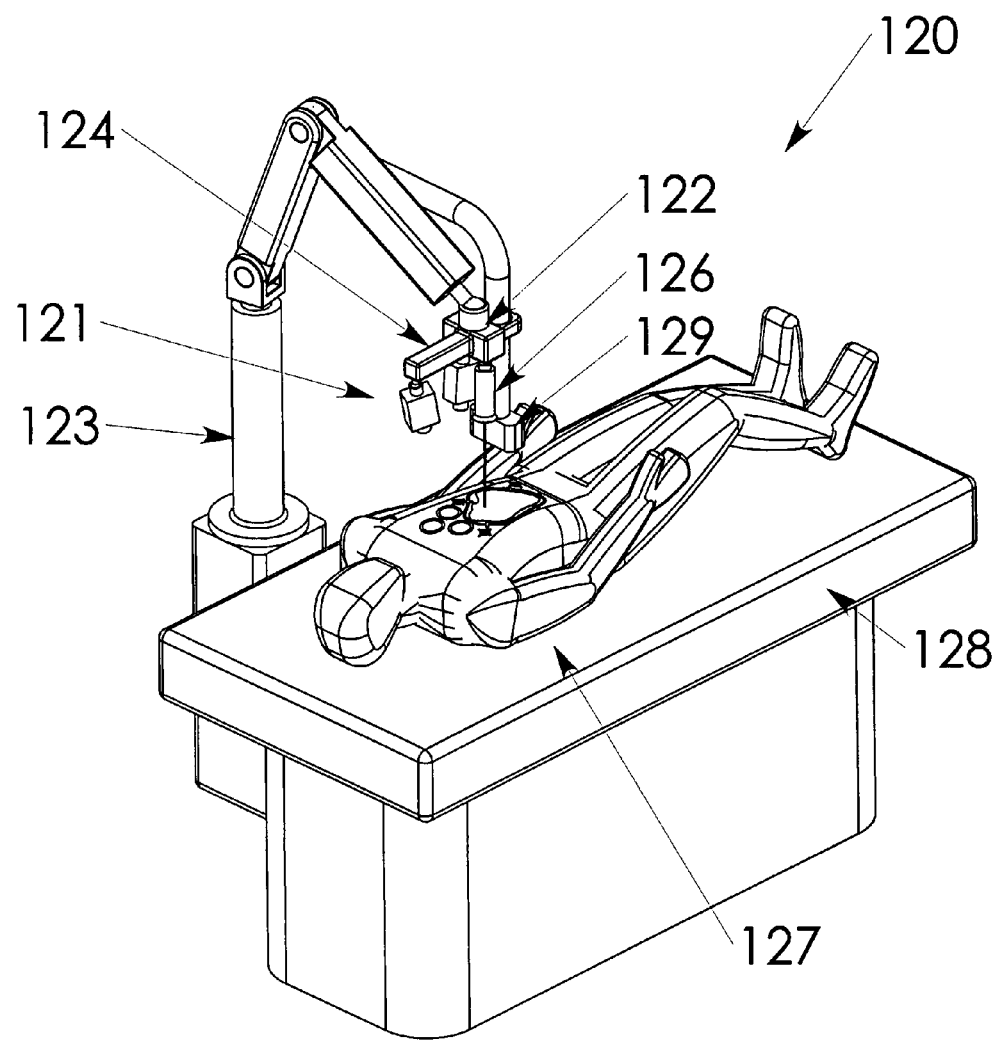
FIG. 3 illustrates a schematic of another embodiment of an automated laser treatment system.
Figure 4:
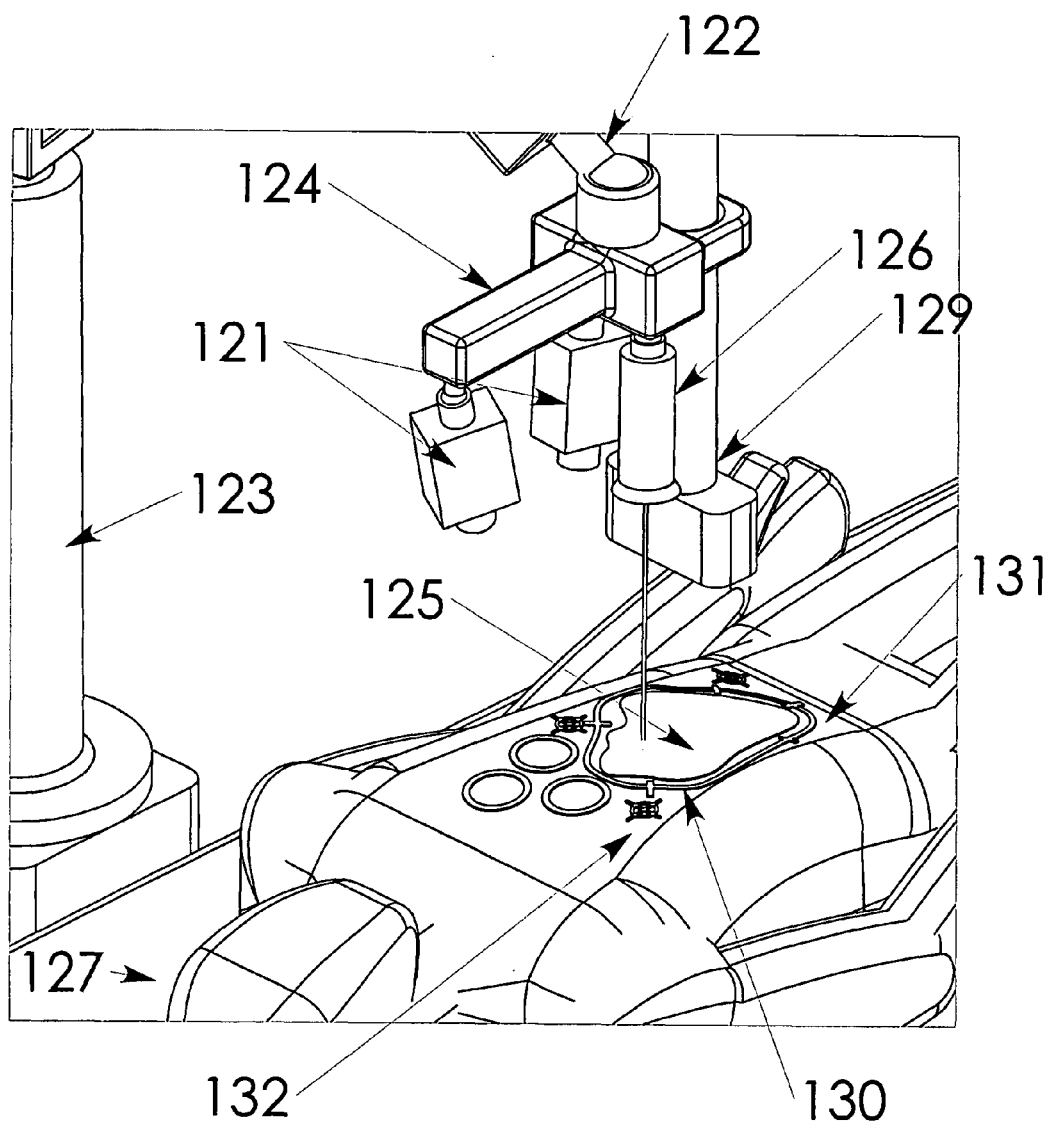
FIG. 4 illustrates a close up view of the treatment area and the main components of the system of FIG. 3.

Another embodiment of the present invention is shown in the schematics of FIG. 3, a close-up of which is shown in FIG. 4. This embodiment of the automated Er-YAG laser debridement system 120 has a configuration that is similar to that of the previous embodiment, except in the positioning of the 3D vision system camera and projector unit 121. In this system configuration, the 3D vision system camera and projector unit 121 is attached to the end-effector 122 of the robot manipulator 123 via an extension structure 124 which allows it to be positioned at a far enough distance from the treatment surface area 125 to provide it with a wide enough field of view to allow a relatively large field of view to accommodate larger treatment areas. This embodiment of the present invention preferably would also use a commercially available Er-YAG laser head system 126 (such as the Profile Surgical Laser system from Sciton, Inc., Palo Alto, Calif.), which is similarly attached directly to the end-effector 122 of the same robot manipulator arm 123. This embodiment would also tolerate a relatively large movement of the patient 127 during the treatment.

A smoke evacuation vacuum head 129 is provided to evacuate the generated smoke and debris resulting from the debridement or other operations. Such smoke evacuation systems are well known in the art and may use air circulation to increase the efficiency of the evacuation system. The evacuated flow is usually filtered using appropriate filtering systems that are routinely cleaned and their filters replaced when such disposable filters are utilized. The smoke evacuation head 129 can be attached to the end-effector 122 of the robot arm 123, directly or through the extension structure 124. The advantage of having the smoke evacuation vacuum head 129 in a fixed position relative to the laser head 126 is that it would then almost always be in a proper position to evacuate the generated smoke. This is compared to the positioning of the smoke evacuation vacuum head 111 in the embodiment of FIGS. 1 and 2, in which it is fixed to the bed 113, and therefore it may have to be repositioned during the treatment for proper evacuation of the generated smoke and debris.

This embodiment of the present invention has the following configuration, characteristics, advantages and shortcomings relative to the other embodiments disclosed herein:

1. An advantage of the present embodiment 120 over the previous embodiment 100 is that in this system configuration, the laser head 126 position is fixed relative to the position of the 3D vision system 121, i.e., its position is fixed in the "global" coordinate system of the 3D vision system 121 (and vise versa), thereby the need for continuous laser head 126 position and orientation calibration relative to a (global) coordinate system of the 3D vision system 121 (or vise versa) is eliminated. It is noted that a "global" coordinate system may alternatively be fixed to the laser system 126, or the robot manipulator arm 123, to the bed 128 or patient 127, and in fact may be arbitrarily positioned. However, since the 3D vision system 121 provides the means of all surface and other positioning and orientation measurements, it is preferred to have a global coordinate system be fixed in the said 3D vision system 121 and all position and orientation, surface, curve, point, etc., measurements be described in this coordinate system. This would in general reduce overall measurement and calculation errors, complexity and increase computational speed. In addition, the position and orientation of the laser head 126 and thereby the laser spot over the treatment surface is more accurately known at all times. The complexity of the system software is also reduced, while the system safety is enhanced. The position of the laser head 126 in the 3D vision system 121 coordinate system may still be checked frequently to test the proper operation of the laser scanning head 126 and its accidental misalignment.

2. The main shortcoming of the system configuration of this embodiment 120 as compared with that of the previous embodiment 100 is that the laser head 126 may at times block the field of view of the 3D vision system 121 over the entire treatment area 125. This is not in general an issue since the immediate areas, most of the circumscribed curves 130, tick marks 131, markers 132, etc., are always in the field of view of the vision system, and the entire treatment area 125 is readily scanned prior to the treatment process. The entire treatment area 125 may also be updated by occasional movement of the end-effector 122 of the robot arm 123 above the entire treatment area 125 followed by resumption of the treatment process.

The end-effector extension structure 124 of the present embodiment of the automated Er-YAG laser debridement system is preferably provided with several attachment points (not shown) for the 3D vision system camera and projector unit 121, providing several choices for the positioning of the 3D vision system 121 relative to the laser head 126. This simple capability would allow this embodiment of the present invention to be used for a wide range of treatment area 125 sizes, including very small treatment areas, for which the 3D vision system 121 will be positioned at a minimum distance to provide maximum surface detail and laser scanning 126 precision, preferably placing it up and by the laser head 126 itself.

Figure 5:
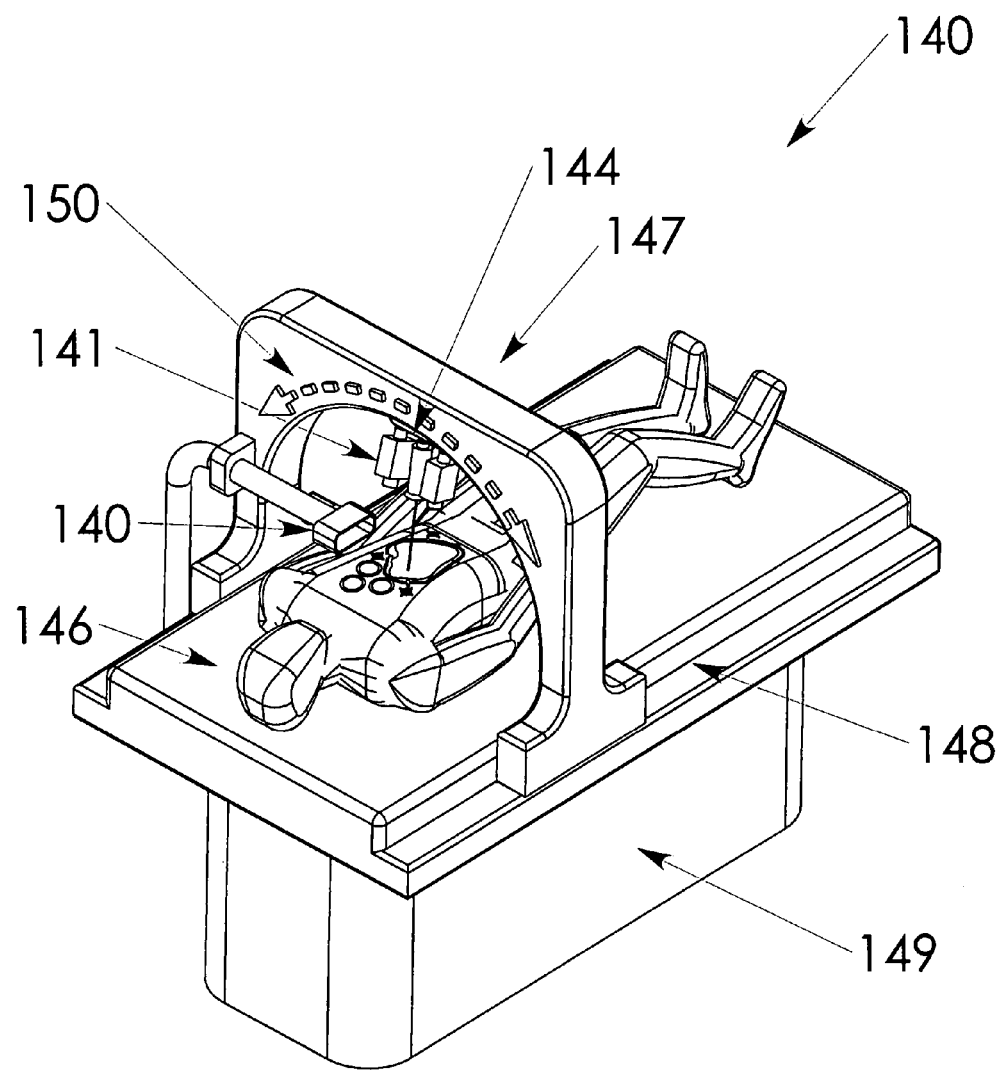
FIG. 5 illustrates a schematic of yet another embodiment of an automated laser treatment system.
Figure 6:
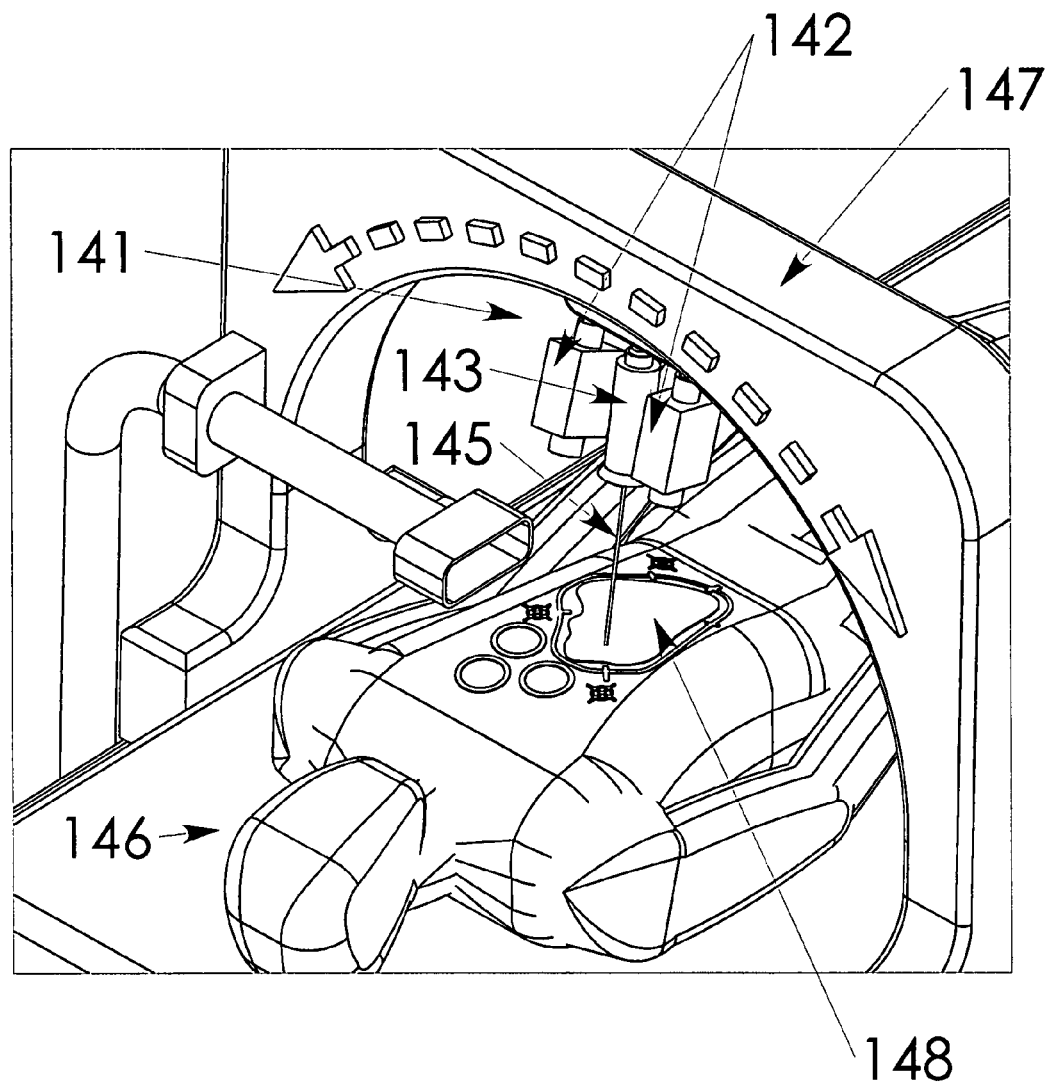
FIG. 6 illustrates a close up view of the treatment area and the main components of the system of FIG. 5.

Yet another embodiment is shown in the schematics of FIG. 5, a close-up of which is shown in FIG. 6. In this embodiment 140 of the automated Er-YAG laser debridement system, a custom designed Er-YAG laser scanning head with integrated vision system camera and projector 141 is employed.

It is noted that in the schematics of FIG. 6, the above three components of this integrated unit, i.e., the laser head 143 and the 3D vision system camera and projector 142, are shown individually as mounted on a single base 144 (FIG. 5) for the sake of illustration clarity. The laser head 143 uses a commercially available Er-YAG laser source and its laser beam is delivered via a fiber optic cable (not shown). A commercially available motorized mirror based scanner or the like (not shown) can be used to scan the laser beam 145 two-dimensionally with the pattern synthesized by the system control computer. Such motorized mirror based scanners that could be used include those commercially available from Blue Hill Optical Technologies, located in Norwood, Mass. or Nutfield Technology, Windham, N.H.

The laser head and vision system camera and projector unit assembly 141, hereinafter collectively called as the "Integrated Laser Scanning and Real-Time Vision System" or ILSRTV system, is attached as can be seen in FIGS. 5 and 6 to a gantry type frame 147 that is positioned above the patient 146 over the area to be treated 148.

In one embodiment of this invention, the frame 147 and the base rail (or the like) 148, which is fixed to the treatment bed 149, form a gantry type of robotic manipulation system. The ILSRTV system 141 is then mounted on a guide fixed to the frame 147 (not shown), which would allow it to be positioned over a range of positions shown as dashed line 150 that can arbitrarily position the laser head and the ILSRTV system 141 along the desired length of the patient 146 body.

Alternatively, the ILSRTV system 141, FIG. 5, is moved over its range of positions 150 by a motor controlled by the (robotic) system control. Alternatively, the ILSRTV system 141 is moved manually along its range of positions 150 and preferably locked in position. Alternatively, when the treatment area 148 is either relatively small or the patient 146 can be moved after treatment of a portion of the body surface to be treated, the ILSRTV system 141 may be fixed to the gantry frame 147.

In FIGS. 5 and 6, the ILSRTV system 141 is shown to consist of a single laser head 143. Alternatively, more than one such laser heads 143 may be used (preferably with one source for the one or more lasers used) to cover significantly larger treatment surface areas 148 than is possible with a single laser head 143. The one or more laser sources are preferably routed selectively to the desired laser head 143 using well known optical switching circuitry. It is noted that with several scanning heads and a single laser source (for each laser type used) the system could cover very large treatment surface areas (or alternatively reduce the maximum required ILSRTV system distance to the treatment area). When very large treatment areas are to be treated with multiple laser heads 143, then more than one set of 3D vision system camera and projector 142 may be required to cover the entire treatment areas with the desired precision.

It is appreciated by those familiar with the art that even though an arc-type and two rail gantry system is shown in the schematics of the embodiment 140, any other gantry type (such as one rail type) or any other type of such robotic system may be used instead. This embodiment can be suitable for hospitals or other similar settings due to the total size and weight of the system. The gantry system can be integrated into the structure of the bed.

The primary advantage of the embodiment 140 over the embodiments 100 and 120 is that the geometric relationship of the 3D vision system camera and projector system 142 with the laser scanner head 143 is fixed in the ILSRTV system and pre-calibrated. Once the treatment area 148 and its 3D geometry are determined, a simple algorithm is used to plan the scanning path of the laser beam 145. During the treatment process, the scanning path of the laser beam 145 is constantly corrected to account for potential body motions of the subject as previously described.

This embodiment has the following configuration, characteristics, advantages and shortcomings relative to the other embodiments:

1. The laser head 143 is preferably fabricated by integrating available Er-YAG and other laser sources when necessary and a visual spotting laser source and a commercially available galvanometer type scanner. The scanning pattern can then be readily and automatically synthesized by the system control computer. Similar computer controlled scanning heads are commonly used in a wide range of applications and the related art is well known.

2. Once the treatment area 148 and its 3D geometry is mapped by the 3D vision system and the physician has interactively indicated the various regions to be scanned and the corresponding laser scanning parameters, a simple algorithm is used to plan and synthesize the scanning path of the laser beam 145 over the indicated treatment area(s) 148.

3. During the treatment process, the scanning path of the laser beam 145 is constantly corrected to account for potential movement of the patient 146 body. High-speed correction is possible due to the near real-time nature of the 3D vision system 142.

4. Since the laser head 143 is positioned farther away from the treatment surface area 148 as is the case for the previous embodiments 100 and 120, in which the laser heads 108 and 126 are designed for hand operation, relatively large surface areas 148 can be treated from a single positioning of the laser head. For example, it should be possible to treat an area with a diameter of over 10-12 inches or more from a distance of around 10-12 inches. The possible range of ILSRTV system 141 distances to the treatment areas 148 and the maximum surface area that can be covered within an acceptable deviation of the laser beam 145 from the direction of normal to the treatment surface 148 are described in more detail later in this disclosure.

5. For systems that are to cover very large areas of the patient body, for example the entire length of the patient body, the robotic gantry system (147 traveling along the rail(s) 148) will require only two degrees-of-freedom; one corresponding to the motion of the gantry arch 147 along the length of the bed 149 over the rail(s) 148, and the second corresponding to the positioning of the base 144 of the ILSRTV system 141 along the gantry arch (as shown in dotted line in the schematic of FIG. 5).

As described above, in one alternative of the embodiment shown schematically in FIGS. 5 and 6, the longitudinal positioning of the gantry arch 147 (for example along the guide 148 or at discrete longitudinal positioning) is manual. The arch can be locked at each of its desired longitudinal positioning before the treatment process is initiated. The positioning of the base 144 of the ILSRTV 141 over the gantry arch 147 can be automated. Alternatively, a permanent or temporary guide for the longitudinal motion of the arch 147 may not be necessary, particularly if the patient 146 is restrained or is not conscious. For relatively small movements, due to the near real-time operation of the present 3D vision system, the feedback loop of the laser beam control system is capable of ensuring proper scanning of the indicated treatment areas 148. For increased safety, a second vision system camera may be used to monitor the error between the actual and the programmed positioning of the laser spot over the treatment area and turn the power to the treatment laser(s) off in case the error is more than a specified threshold. Additional safety can be provided via a tri-axial accelerometer (or another similar motion sensory device) based safety switch, which would shut the laser power off when a sudden movement of the ILSRTV system 14 is detected. Such a capability would prevent accidental exposure if some object or person collides with the arch 147 and/or the ILSRTV system 141 or their wiring, which could result in a sudden movement of the laser beam before the 3D vision system 142 (or aforementioned additional vision camera) has a chance to detect it. Such tri-axial accelerometers can be readily integrated into any of the embodiments disclosed herein.

A second alternative of the embodiment shown schematically in FIGS. 5 and 6 is identical to the above first alternative with the exception that the adjustment of the position of the base 144 of the ILSRTV system 141 over the gantry arch 147 is performed manually, using any one of the well known means, such as guide and carriage type. This manual adjustment capability may, however, be motorized. Means of locking based to the gantry arch can be provided to minimize the possibility that the ILSRTV system 141 is accidentally moved during the treatment process due to an object or person striking it or for any other reasons. The system is preferably equipped with the aforementioned sudden motion detection capability sing accelerometers or other similar motion detection sensors.

This alternative embodiment may be fabricated with a very lightweight arched central rail, supported by a collapsible side support "legs" that can be quickly deployed and locked in place, and which could be collapsed to fit into a relatively small carrying case. The entire system would then be very portable, while being capable of covering the specified treatment area at each setting.

In yet another alternative of the embodiment shown schematically in FIGS. 5 and 6, the system is identical to the above first alternative with the exception that the base 144 of the ILSRTV system 141 is attached directly to a manually adjustable floor stand, preferably one that is provided with locking wheels. The system can then be readily moved to the desired position relative to the patient and locked in place. The floor stand is preferably provided with an articulating arm to allow proper positioning of the ILSRTV system 141 over the treatment area 148. Such an embodiment is described in detail below. It is noted that the described embodiment is particularly suitable for debridement of chemical and thermal burns.

It is, however, appreciated by those familiar with the art that numerous other similar alternatives are possible for the embodiments 100, 120 and 140 shown in the schematics of FIGS. 1-6 and their aforementioned alternative embodiments. These obviously include those obtained by combining various features of one or more of these embodiments. In addition, and generally at the cost of increasing system complexity and cost, more than one scanning head (preferably using a single laser source) and/or 3D vision systems could be employed to significantly increase the visual coverage and the treatment area coverage with minimal or no movement of the laser head and/or the 3D vision system. Additional cameras (and/or 3D vision systems) may also be used to provide added means for very rapid sensing of the laser beam spot position error during the treatment and/or to provide an overall (macro and generally coarse and less precise) vision of the patient and the treatment areas, the laser head, the 3D vision system, the attending personnel, etc., for reasons such as overall safety.

Figure 7:
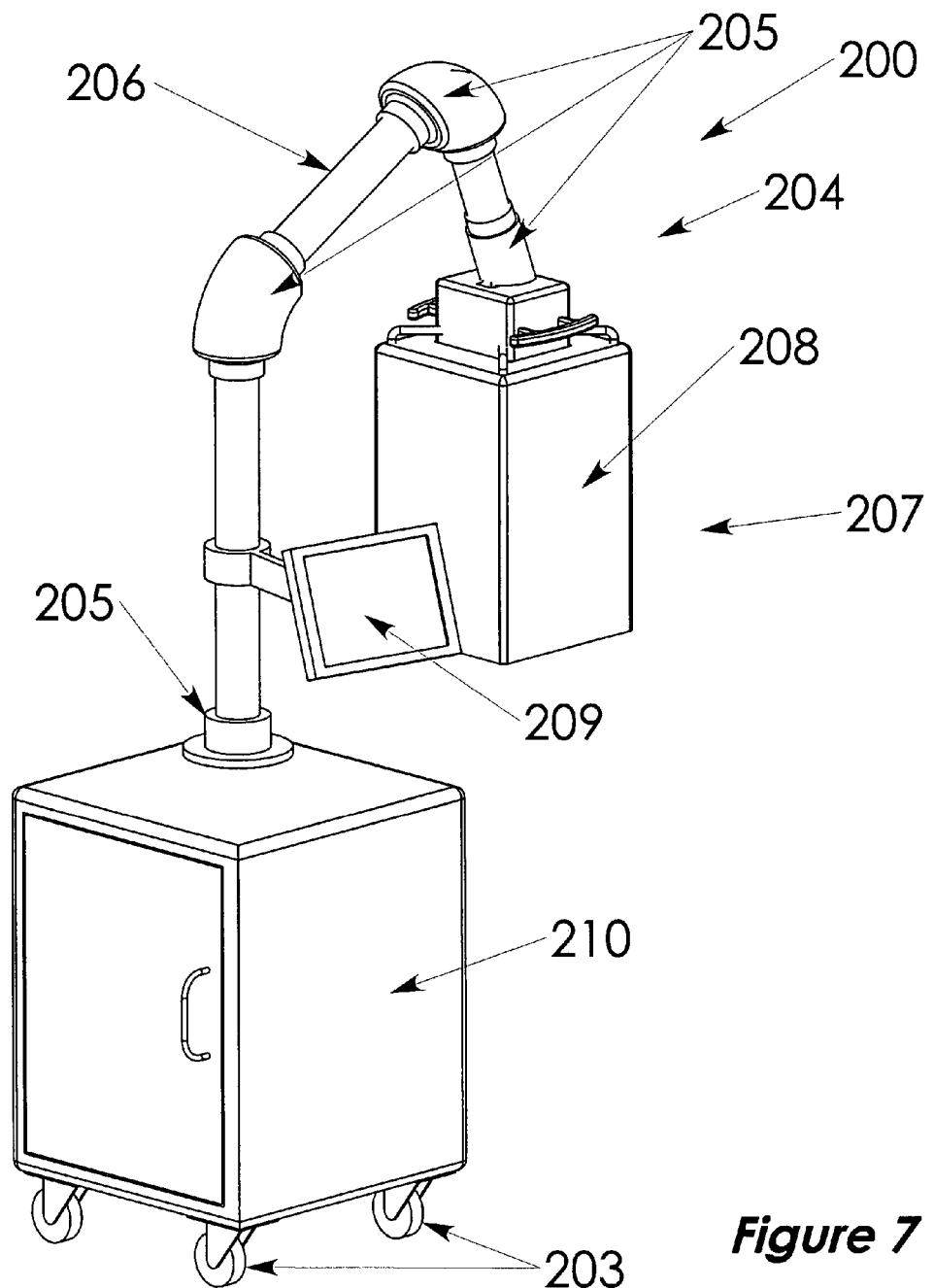
FIG. 7 illustrates a schematic of still yet another embodiment of an automated laser treatment system.
Figure 8:
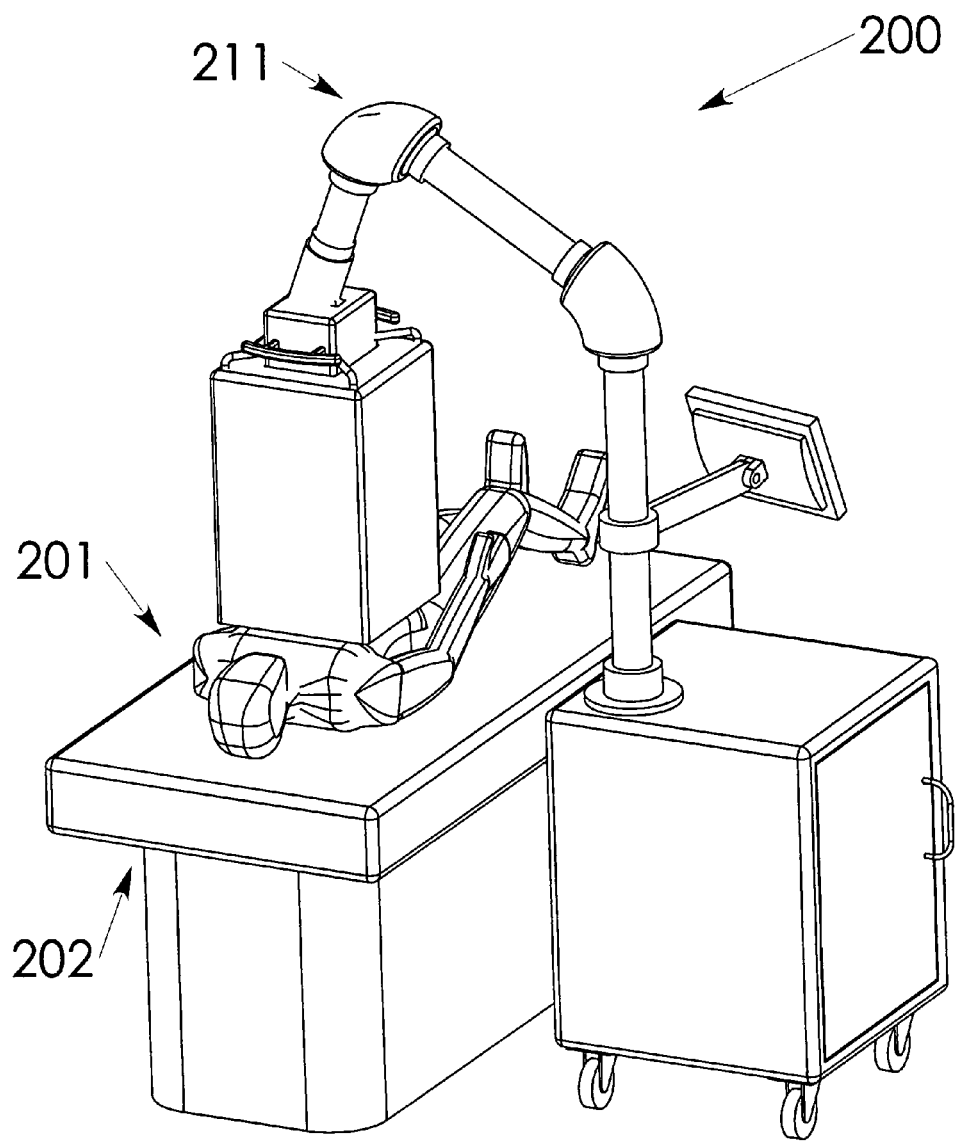
FIG. 8 shows the system of FIG. 7 positioned for treatment of a patient.

Still yet another embodiment 200 of the present invention is shown in FIG. 7. FIG. 8 shows the general positioning of the embodiment 200 during the treatment of a patient 201 laying over the bed 202. The system 200 is designed to be self-contained, requiring only electrical power for operation. The system 200, with its articulating arm stowed over the base cabinet, can be readily stored or moved to a side until it is needed again. The setup of the system 200 will generally proceed as follows:

1. Wheel the system 200 into approximate position and lock wheels 203.
2. Grasp treatment head handle(s) 204 and depress button (not shown) to unlock joints 205 of articulating arm 206. Such articulating arms are well known in the art.
3. Position treatment head 207 such that the bottom periphery of the laser shield 208 is close to the patient 201 and envelopes the desired treatment area.
4. Position the LCD touch screen 209 in a convenient location such that the user may interface with the patient 201 and the computer simultaneously.

The base cabinet 210 for the laser debridement system 200 serves three main functions. Firstly, equipped with wheels 203, preferably of locking caster type, the cabinet 210 provides for easy transport of the system 200 and for secure placement near the bed 202 with the patient 201. Secondly, the cabinet 210 is massive and acts as a counterbalance to prevent the system 200 from tipping over when the articulating treatment arm 206 is extended over the patient 201. Finally, the cabinet 210 houses many of the larger, heavier components of the system 200. Placing these components within the cabinet 210 helps to increase the stability of the system 200 and also isolates the components from the operating theatre and vice-versa. The main components contained within the cabinet 210 are:

1. A computer, preferably of PC type, which controls the 3D vision and laser scanning systems.
2. The laser sources and their power sources and cooling systems if any (described later in this disclosure).
3. The vacuum generator for the smoke evacuation system (described later in this disclosure), preferably equipped with a HEPA filtration system.

The articulating arm 206 of the laser debridement system 200 serves three main functions. Primarily, the arm provides a means by which the treatment head 207 may be positioned over a patient 201 laying on a standard operating table 202. The articulating arm 206 is preferably provided with automatic-locking (preferably rotary) joints, counterbalance springs (not shown), and a release button located on the handle 204 of the treatment head 207. The articulating arm 206 is preferably provided with at least four rotary joints to allow the positioning of the treatment head in an arbitrary position over the treatment area. Such articulating arms 206 and their aforementioned components are well known in the art.

When the handle 204 of the treatment head 207 is grasped and the release button depressed, the joints 205 of the articulating arm 206 are unlocked and the counterbalance springs provide stability while the operator positions the treatment head 207 over the treatment area of the patient 201. Upon release of the button and handle, the joints 205 of the articulating arm 206 lock the articulating arm in position automatically. The (rotary) joints are provided with bellows 211 to prevent contaminants in the joints from entering the operating theater and vice-versa, and to provide a smooth wash-down surface for regular cleaning and sterilization. One of the joints 205 is preferably a single parallel-axis rotary joint which attaches the articulating arm 206 to the base cabinet 210 may be outfitted with an appropriate lip seal to provide the same functions as the bellows on the other joints 205.

The secondary function of the articulating arm is to provide a conduit through which the 3D vision system cables, laser fiber optic cables, and the vacuum tubing for the smoke evacuator can be routed from the base cabinet 210 to the treatment head 207. Like the bellows 211, this cable and tube routing is to provide a smooth, continuous surface for regular cleaning of the articulating arm. Finally, the articulating arm may also be used to support the (preferably swiveling cantilever) mount for the LCD touch screen 209. This type of screen and mounting is chosen to offer the operator a slender interface with the computer which can be positioned at any convenient orientation and operated with a stylus to avoid touching the screen directly.

Figure 9:
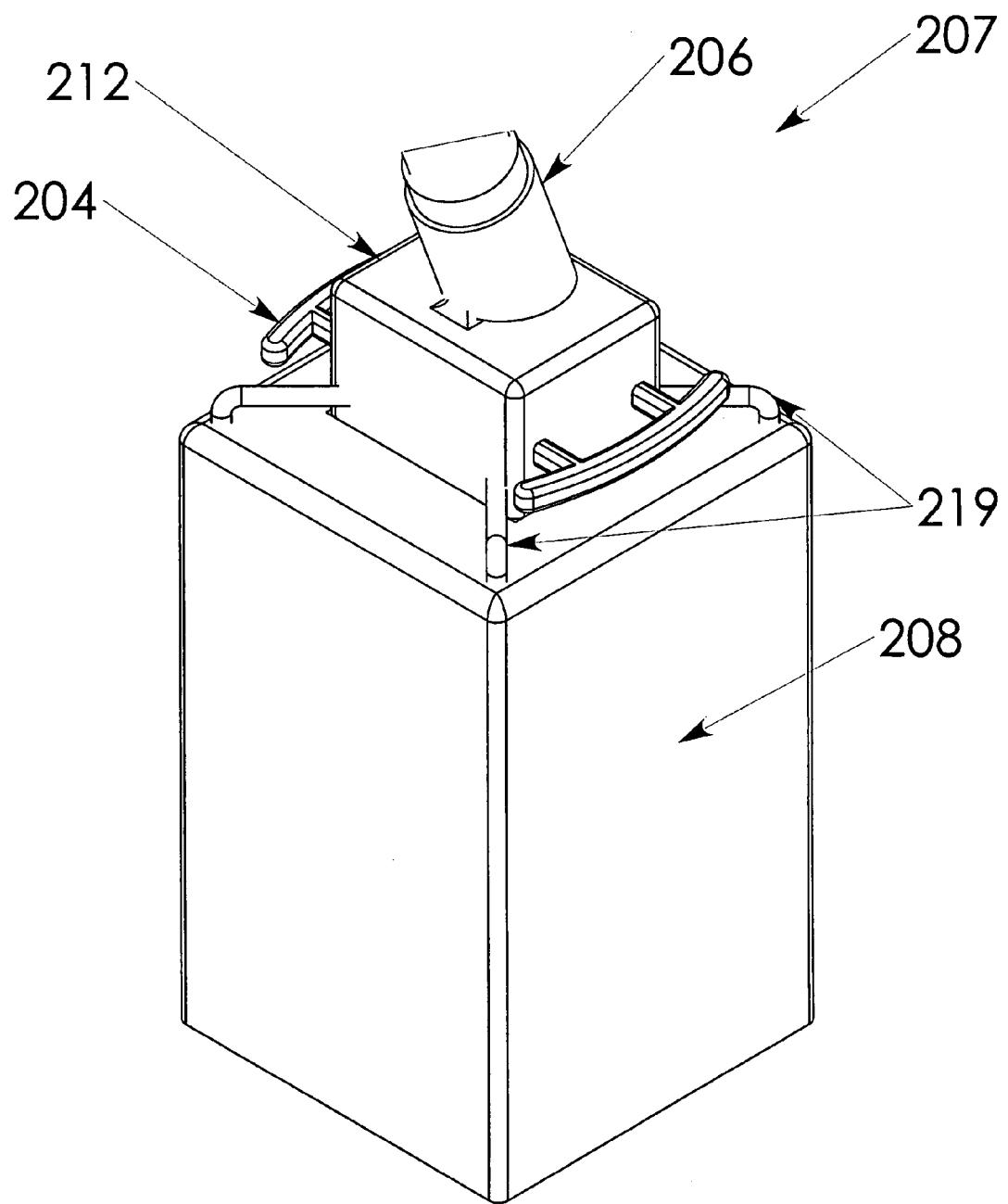
FIGS. 9 and 10 illustrate the treatment head of the system of FIG. 7.
Figure 10:
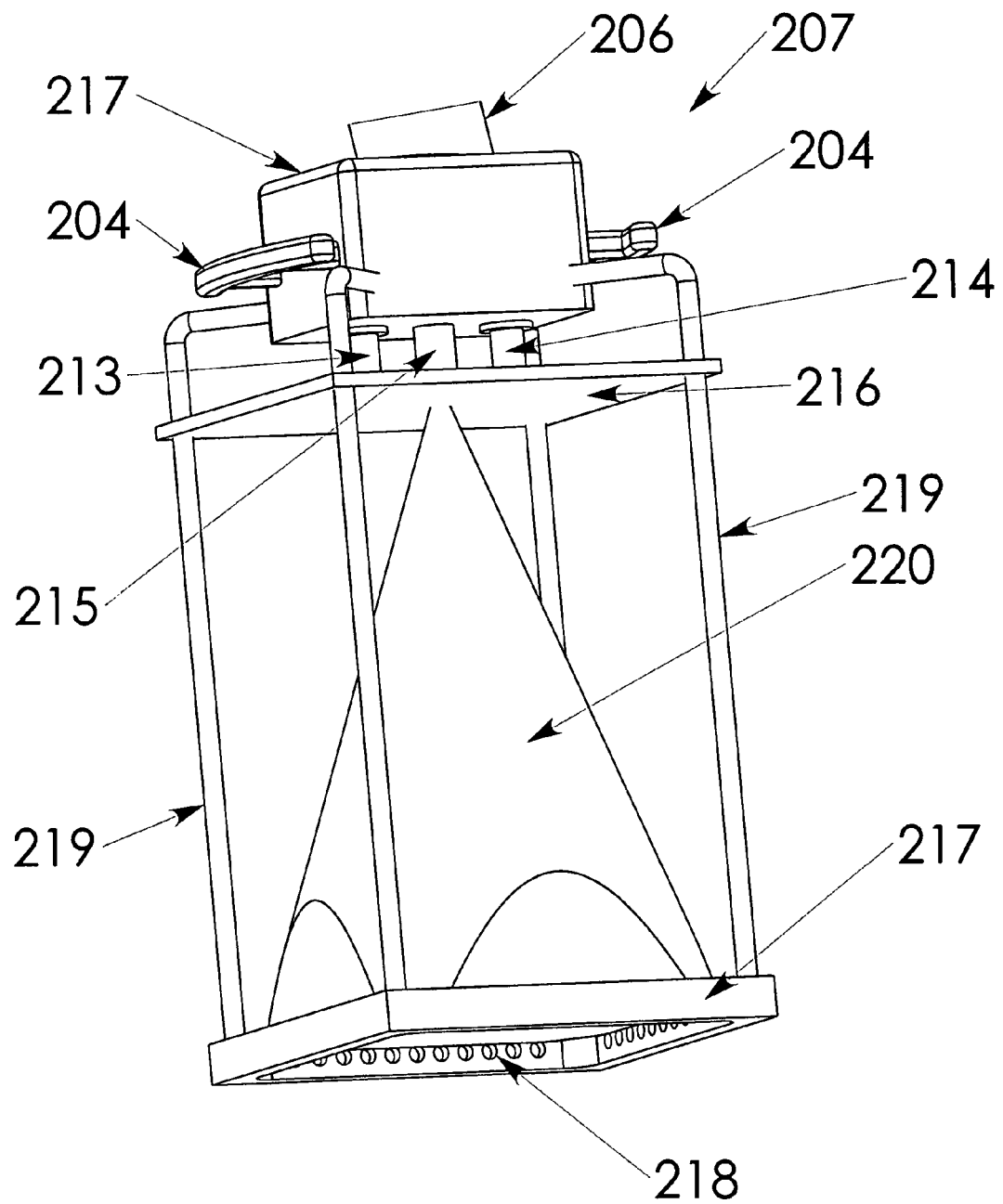

The details of a typical treatment head 207 design with and without the laser shield 208 is shown in FIGS. 9 and 10, respectively. The treatment head 207 is attached to the end of the articulating arm 206 as shown in FIGS. 7-10. The treatment head 207 consists of the aforementioned ILSRTV system 212, consisting of the 3D vision camera 213 and projector 214, and laser scanning housing 215; two handles 204; a laser shield 208, opaque to the wavelengths of the treatment lasers and otherwise visually transparent; a protective (top) glass plate 216 which is preferably fabricated or coated to be opaque to the wavelengths of the treatment lasers and otherwise visually transparent; and smoke evacuation manifold 217 with evacuation openings 218 and ducts 219. Also shown is the conical workspace 220 of the laser scanning head 214. A conical workspace with a cone angle of 20-40 degrees is generally preferred. Clearly, with the attachment of different shield assemblies, a plurality of treatment area sizes and shapes can be realized.

As it is shown in FIG. 10, the ILSRTV system 212 housing contains the 3D vision camera 213 and projector 214 and laser scanning housing 215, and serves as a thoroughfare for routing the smoke evacuation tubing 219 through the articulating arm 206, back to the HEPA filter (not shown) in the base cabinet 210 (FIG. 10). The protective glass plate 216 is provided to protect the ILSRTV system 212 from contamination from any smoke or other debris which is not immediately collected by the smoke evacuation system.

The laser shield 208 prevents any errant directions or reflections of the treatment laser(s) from exiting the treatment head 207. When positioned as close as practical to the patient 208, FIG. 8, any unacceptable gaps in the laser shield 208 may be blocked with smaller sheets of protective laser-blocking material (preferably movable panels—not shown). The shield also provides a chamber to contain smoke or other debris which is not immediately collected by the smoke evacuation system, and serves as a hard-guard to prevent the operator or other bystanders from accidentally crossing the path of the (mostly invisible) treatment laser beams during treatment.

The laser beam is preferably delivered via a fiber optic cable (not shown) to the scanning head as it is commonly done in the art. For laser beam scanning, a galvanometer based scanner is preferably used as previously indicated, which allows for the laser beam to be scanned two-dimensionally in any arbitrary pattern. This capability is important because burn areas are most likely in irregular shapes. Being able to scan in any arbitrary pattern prevents healthy tissues from being removed.

The 3D vision system projector 213 and (CCD) camera 214 are connected to the system PC (not shown) but located in the base cabinet 210. As previously described for previous embodiments of the present invention, the 3D vision system automatically locates the circumscribing curve and its position tick marks and markers (see for example FIG. 4) and determines the coordinates of the treatment area for laser scanning. During the treatment process, the circumscribing curve and associated position tick marks and markers (if any) are constantly monitored by the vision system for signs of significant body movement. When significant body movement is detected, the coordinates of the laser scan area are updated to compensate for the body movement and the process continues. The position of the laser spot on the surface of the treatment area is similarly measured and compared to its expected position and used to correct its positioning and if the error exceeds a set threshold, then power to the treatment laser is shut off and a warning message is sent to the control monitor 209, and preferably a warning light is lit and/or an audio warning sound is activated.

To ensure accurate scanning of the laser beam based on the coordinate information provided by the 3D vision system, the geometric relationship between the laser scanner and the 3D vision system needs to be accurately determined. This is accomplished through calibration, which is aimed at determining the equation of the laser beam as a line in the coordinate system of the vision system. However, since this geometric relationship is fixed, once the calibration is done, the system will maintain its accuracy for as long as this geometric relationship is maintained. In such systems, system calibration is periodically checked and recalibration is made whenever it is determined to be required.

As discussed above, the need to manually mark the burnt area in need of debridement can be eliminated by the use of a recognition system which can differentiate the burnt area from healthy tissue. Recognition systems for recognizing burnt tissue are known in the art.

One of the largest uses for lasers in dermatology is the removal of tattoos. The systems disclosed herein can operate for use in removing tattoos. The laser heads can have various lasers for use with specific colors of the tattoo. Besides the marking and tic marks disclosed above, the system can use a recognition system to detect the colors in the tattoo and selectively and automatically remove the tattoo by destroying tattoo pigment without causing much damage to the surrounding skin. The altered pigment is then removed from the skin by scavenging white blood cells, tissue macrophages. The choice of laser depends on the color, depth and chemical nature of the tattoo ink. The present system allows for automatic switching between different lasers depending on the color pigment detected.

Lasers have also become very popular to remove excessive hair. Laser treatments remove dark hair quickly and it may take 3 to 6 months before regrowth is evident. Such laser treatments are less painful and much quicker than electrolysis. In current systems, a physician or highly trained technician tediously identifies each of the unwanted hairs and manually directs a laser to the hair. Alternatively, the technician directs the laser to an entire surface, regardless of whether hair follicles are present. Several treatment cycles are required with the spacing between treatments dependent on the body area being treated. The dark hair (usually nubs that are recently shaved) can be easily recognized with a computer recognition system and targeted by the automated laser system. The disclosed automated system can eliminate the need for a physician or highly trained technician and greatly speed up the process.

Pulsed $CO_2$ and erbium:YAG lasers have been used successfully in reducing and removing facial wrinkles, acne scars and sun-damaged skin. Typically a 50% improvement is found in patients receiving $CO_2$ laser treatment. The disclosed automated system can greatly speed up the process, particularly by the provision of recognition algorithms. Again, a recognition system can be used to recognize the facial wrinkles, acne scars and sun-damaged skin to eliminate the need to manually mark the same.

There are also some skin scaling and sclerosis conditions, which would need entire body treatment (in some cases they use the light scanning to activate the drug on the skin surface). The systems disclosed herein can provide a whole body treatment that would generate a real-time 3D image of the body surface and then scan all the affected areas as indicated by the physician. Alternatively, the affected areas can be automatically located by a vision system. In either case, the real-time surface measurement information is used by a controller to control the laser scanning to treat the affected areas.

For the last decade, lasers have been used in the fight against aging skin. Laser resurfacing is a very controlled burning procedure during which a laser vaporizes superficial layers of facial skin, removing not only wrinkles and lines caused by sun damage and facial expressions, but also acne scars, some folds and creases around the nose and mouth, and even precancerous and benign superficial growths. In a sense, the laser procedure creates a fresh surface over which new skin can grow. Collagen is a key fibrous protein in the skin's connective tissue, and it helps give the skin its texture. Natural aging and such factors as sun damage and smoking help break down the collagen layer so that the skin's once smooth surface develops wrinkles. New, more youthful collagen actually forms after laser treatment. The disclosed automated laser debridement system can readily map the face of the patient and recognize and eliminate areas where laser surfacing is not needed, for example, above the hairline, the lips, the eyes and eye lids, eyebrows and other facial hair areas. Furthermore, other features, such as around the lips and nose, can be automatically identified. The identified portions of the patients face, other than the excluded areas can then be laser resurfaced automatically without the need for constant monitoring by an attending physician or medical technician.

However, perhaps the largest group of patients who can potentially benefit from cosmetic laser procedures are those with scars resulting from surgery. In the U.S. alone, the ongoing surgical caseload produces more than 50 million incision sites annually that can benefit from early intervention with laser treatment (a C-beam pulsed dye laser has been found to be effective on scar tissue). This is a larger patient population than any other group in the aesthetic laser field. It includes all plastic surgery (particularly facelifts), abdominal, breast, Cesarean sections, sternotomies, small telltale scars from liposuction and other less invasive procedures, and others. The novel automated laser debridement system disclosed above can recognize scar tissue, such as by the differences in certain image characteristics of the scar tissue as compared to healthy tissue and control the robot arm to direct the laser only at such scar tissue.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. An automated system for debriding a burned portion of skin with a laser, the automated system comprising:
    an identification system for identifying a boundary outlining the burned portion of the skin to be debrided;
    a computer vision system having a three-dimensional surface mapping vision system for generating a real-time three-dimensional model of the identified area of the burned portion of the skin inside the boundary;
    a monitor for displaying the three-dimensional model of the identified area of the burned portion of the skin inside the boundary on a touch screen display;
    a laser system having a laser head for directing a treatment laser to the identified area of the burned portion of the skin inside the boundary;
    an input device for entering operating parameters of the laser system;
    a movable member coupled to the laser head for directing the laser within the area of the burned portion of the skin inside the boundary identified by the identification system and generated by the computer vision system; and
    a controller configured to control the computer vision system to update the three-dimensional model of the identified area in predetermined intervals and to control the laser system and movable member to automatically debride the identified area based on the updated three-dimensional model of the identified area and the operating parameters of the laser system;
    wherein the identification system comprises configuring the computer vision system such that a user can circumscribe the boundary outlining the burned portion of the skin on the monitor using the touch screen display; and
    wherein the controller is further configured to control the computer vision system to continuously update the three-dimensional model with information regarding treated regions of the circumscribed burned portion and a number of passes of the laser head in the treated regions.

2. The system of claim 1, wherein the movable member is a robotic arm.

3. The system of claim 1, wherein the movable member is a gantry.

4. The system of claim 1, wherein the movable member is an articulating arm.

5. The system of claim 4, wherein the three-dimensional surface mapping vision system is provided on a stationary member separate from the movable member.

6. The system of claim 4, wherein the three-dimensional surface mapping vision system is provided on the movable member.

7. The system of claim 1, further comprising a projector for projecting one or more reference markers on the skin to visually confirm the identified area by the identification system.

8. The system of claim 7, wherein the projector is provided on a stationary member separate from the movable member.

9. The system of claim 7, wherein the projector is provided on the movable member.

10. The system of claim 1, further comprising a vacuum system having a vacuum head for evacuating smoke resulting from the interaction of the laser with the skin of the treatment area.

11. The system of claim 10, wherein the vacuum head is provided on a stationary member separate from the movable member.

12. The system of claim 10, wherein the vacuum head is provided on the movable member.

13. The system of claim 1, further comprising a cabinet for storing components of one or more of the modeling system, laser system and movable member.

14. The system of claim 13, where the cabinet further stores one or more of a vacuum system, projector system and controller.

15. The system of claim 1, further comprising an enclosure disposed on the movable member, wherein the enclosure has an open end for contact with the skin in a vicinity of the treatment area, the enclosure containing a camera and the laser head.

16. The system of claim 15, where the enclosure further contains one or more of a vacuum head and projector.

17. The system of claim 16, wherein the vacuum head is disposed at least partially about a periphery of the open end.

18. The system of claim 1, wherein the treatment laser is an Er:YAG treatment laser.

19. The system of claim 1, wherein the treatment laser is a $CO_2$ treatment laser.

20. The system of claim 1, wherein the input device is also the touch screen device of the monitor.

* * * * *